United States Patent
Ming et al.

(10) Patent No.: US 10,742,962 B2
(45) Date of Patent: *Aug. 11, 2020

(54) METHOD AND SYSTEM FOR CAPTURING IMAGES FOR WOUND ASSESSMENT WITH MOISTURE DETECTION

(71) Applicant: KONICA MINOLTA LABORATORY U.S.A., INC., San Mateo, CA (US)

(72) Inventors: Wei Ming, Cupertino, CA (US); Xiaonong Zhan, Foster City, CA (US); Taisuke Akahori, Campbell, CA (US)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/248,302

(22) Filed: Jan. 15, 2019

(65) Prior Publication Data
US 2019/0149803 A1 May 16, 2019

Related U.S. Application Data

(63) Continuation of application No. 15/394,846, filed on Dec. 30, 2016.

(51) Int. Cl.
*H04N 9/47* (2006.01)
*H04N 7/18* (2006.01)
(Continued)

(52) U.S. Cl.
CPC ........... *H04N 13/25* (2018.05); *A61B 5/0077* (2013.01); *A61B 5/445* (2013.01); *A61B 5/7278* (2013.01);
(Continued)

(58) Field of Classification Search
CPC ..... A61B 5/0077; A61B 5/0086; A61B 5/445; A61B 5/7278; G06K 2209/401;
(Continued)

(56) References Cited

U.S. PATENT DOCUMENTS

| 8,923,585 B1 | 12/2014 | Peleg |
| 9,491,441 B2 | 11/2016 | Sarmast et al. |

(Continued)

FOREIGN PATENT DOCUMENTS

| WO | 01/35827 A1 | 5/2001 |
| WO | 2006/040773 A2 | 4/2006 |

(Continued)

OTHER PUBLICATIONS

International Search Report in related PCT application No. PCT/US2017/053624, dated Nov. 27, 2017.

(Continued)

*Primary Examiner* — Jessica M Prince
(74) *Attorney, Agent, or Firm* — Chen Yoshimura LLP

(57) ABSTRACT

A wound assessment method which can estimate a moisture level of the wound, and related image capture device. The wound area is imaged at least twice where the wound is illuminated under different illumination light intensities. The first image captured using a relatively low illumination light intensity is analyzed to assess the wound, for example measuring its size, color and texture. The second image captures using a relatively high illumination light intensity (e.g. using a flash) is analyzed to estimate the moisture level of the wound. The moisture level estimation method extracts white connected components from the second image, and estimates the moisture level based on the number, sizes, and centroid distribution of the white connected components. A 3D image of the wound may also be captured, e.g. using a structured-light 3D scanner of the image capture device.

14 Claims, 5 Drawing Sheets

(51) Int. Cl.
| | |
|---|---|
| *G06K 9/00* | (2006.01) |
| *H04N 13/25* | (2018.01) |
| *H04N 5/235* | (2006.01) |
| *A61B 5/00* | (2006.01) |
| *H04N 13/254* | (2018.01) |
| *H04N 13/257* | (2018.01) |
| *G06K 9/20* | (2006.01) |
| *G06K 9/34* | (2006.01) |
| *G06K 9/38* | (2006.01) |
| *G06K 9/46* | (2006.01) |
| *G06T 7/00* | (2017.01) |
| *G06T 7/50* | (2017.01) |
| *G06T 7/90* | (2017.01) |
| *H04N 5/232* | (2006.01) |
| *G06K 9/62* | (2006.01) |

(52) U.S. Cl.
CPC .......... *G06K 9/2027* (2013.01); *G06K 9/342* (2013.01); *G06K 9/38* (2013.01); *G06K 9/4652* (2013.01); *G06T 7/0012* (2013.01); *G06T 7/0014* (2013.01); *G06T 7/50* (2017.01); *G06T 7/90* (2017.01); *H04N 5/2355* (2013.01); *H04N 5/2356* (2013.01); *H04N 5/23293* (2013.01); *H04N 13/254* (2018.05); *H04N 13/257* (2018.05); *A61B 5/0086* (2013.01); *G06K 9/6218* (2013.01); *G06K 2209/401* (2013.01); *G06T 2207/10012* (2013.01); *G06T 2207/10016* (2013.01); *G06T 2207/10024* (2013.01); *G06T 2207/30088* (2013.01); *G06T 2207/30096* (2013.01)

(58) Field of Classification Search
CPC ........ G06K 9/2027; G06K 9/342; G06K 9/38; G06K 9/4652; G06K 9/6218; G06T 2207/10012; G06T 2207/10016; G06T 2207/10024; G06T 2207/30088; G06T 2207/30096; G06T 7/0012; G06T 7/0014; G06T 7/50; G06T 7/90; H04N 13/25; H04N 13/254; H04N 13/257; H04N 5/23293; H04N 5/2355; H04N 5/2356
See application file for complete search history.

(56) References Cited

U.S. PATENT DOCUMENTS

| | | | |
|---|---|---|---|
| 2012/0059266 A1* | 3/2012 | Davis | A61B 5/445 600/476 |
| 2013/0322711 A1 | 12/2013 | Schultz et al. | |
| 2015/0150457 A1 | 6/2015 | Wu et al. | |
| 2016/0027171 A1* | 1/2016 | Spahn | G01J 5/00 382/128 |
| 2016/0166194 A1 | 6/2016 | Gareau et al. | |
| 2016/0189377 A1* | 6/2016 | Houjou | G06T 7/11 382/133 |
| 2016/0210746 A1* | 7/2016 | Matsuda | G06T 7/0012 |
| 2016/0217341 A1* | 7/2016 | Hung | G06K 9/4642 |
| 2017/0104925 A1 | 4/2017 | Ng et al. | |
| 2017/0154420 A1* | 6/2017 | Barnes | G06T 5/20 |
| 2017/0178322 A1* | 6/2017 | Hakuk | G06K 9/52 |

FOREIGN PATENT DOCUMENTS

| | | |
|---|---|---|
| WO | 2010/103267 A1 | 9/2010 |
| WO | 2013/096766 A2 | 6/2013 |

OTHER PUBLICATIONS

Written Opinion in related PCT application No. PCT/US2017/053624, dated Nov. 27, 2017.

* cited by examiner

METHOD AND SYSTEM FOR CAPTURING IMAGES FOR WOUND ASSESSMENT WITH MOISTURE DETECTION

BACKGROUND OF THE INVENTION

Field of the Invention

The present invention relates to a device and method for capturing images of visible injuries or wounds and for performing wound assessment, and more particularly, it relates to wound assessment with moisture level detection.

Description of Related Art

For many wound types, such as pressure ulcers, recovery times can be very long. To track wound progress and perform proper treatment, the first step is to capture images of the wound properly. Wound images may then be analyzed to measure the size, texture and color of the wound. One useful aspect of wound assessment is estimating the moisture level of a wound. Currently there is no solution to estimate the moisture level of a wound. Also, when a wound has a high moisture level due to blood or pus, it may have a wet and thus shiny wound surface, which makes the wound difficult to properly image; the measurement of a wound with 2D and 3D cameras in such a case is often not stable.

SUMMARY

Accordingly, the present invention is directed to a method for capturing images of a wound that substantially obviates one or more of the problems due to limitations and disadvantages of the related art.

An object of the present invention is to provide a method for properly capturing wound images and measuring the wound dimension and moisture level using an image capturing device alone without using additional measuring devices.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides a method implemented in a system including an image capture device for assessing a wound of a patient, which includes: (a) capturing a first image of a part of the patient's body which contains the wound, the part of the patient's body being illuminated by a light of a first intensity during the capture; (b) capturing a second image of the part of the patient's body, the part of the patient's body being illuminated by a light of a second intensity during the capture, the second intensity being stronger than the first intensity; (c) estimating a moisture level of the wound by analyzing the second image; (d) assessing the wound by analyzing the first image, including measuring at least one of a size, texture and color of the wound; and (e) registering assessment results of the wound, wherein the assessment result includes the estimated moisture level and the at least one of the size, texture and color of the wound.

In a preferred embodiment, the step of estimating a moisture level of the wound includes extracting white connected components in the wound area, and estimating the moisture level of the wound based on a number of the white connected components, sizes of the white connected components, and a distribution of locations of the white connected components.

In another aspect, the present invention provides an image capture device which includes: a 2D camera for capturing two-dimensional images; a 3D camera for capturing three-dimensional images; a user interface screen for displaying images and information and for interacting with a user; a processor; and a computer usable non-transitory memory having a computer readable program code embedded therein which is configured to be executed by the processor to control the 2D camera, the 3D camera, and the user interface, and to perform the above described process of assessing a wound of a patient.

It is to be understood that both the foregoing general description and the following detailed description are exemplary and explanatory and are intended to provide further explanation of the invention as claimed.

DETAILED DESCRIPTION OF PREFERRED EMBODIMENTS

Figure 1:
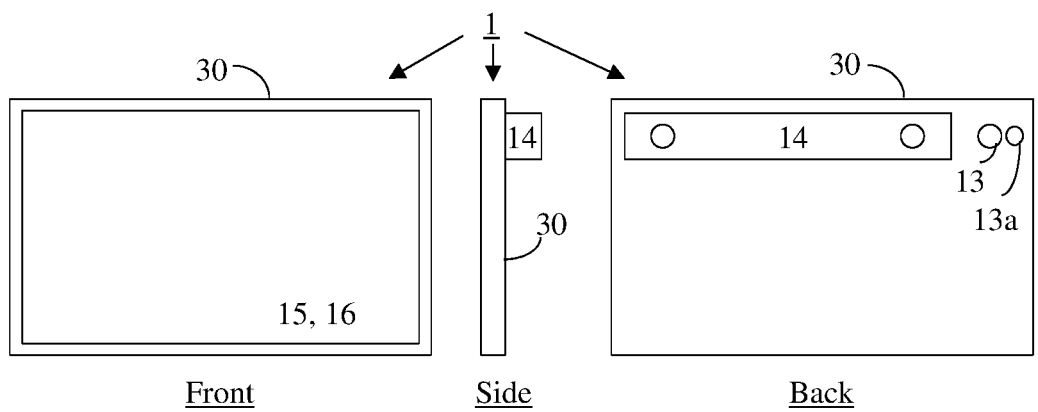
FIG. 1 is an illustration of an imaging device for wound assessment with a graphical user interface in accordance with an exemplary embodiment.
Figure 2:
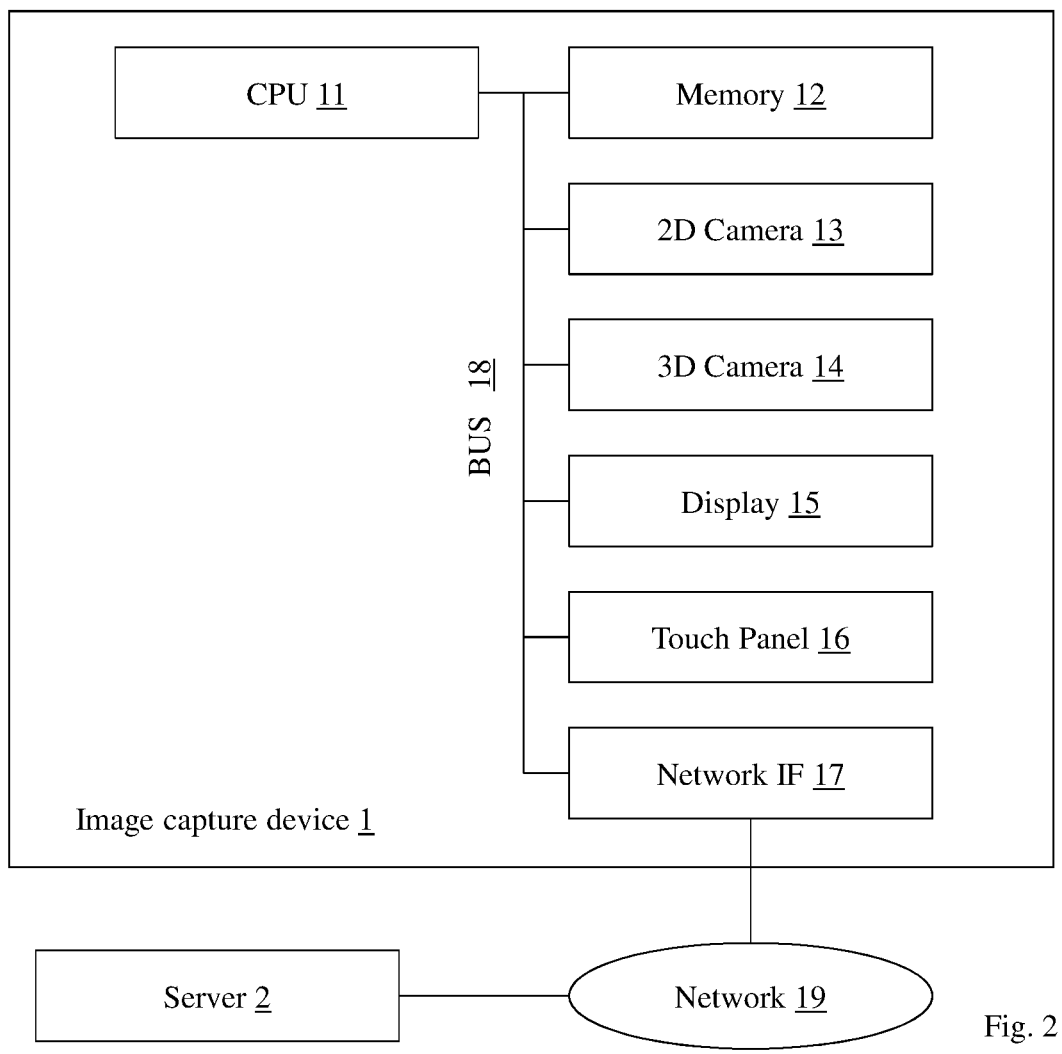
FIG. 2 is a schematic hardware block diagram showing the structure of the imaging device of FIG. 1.

FIG. 1 is an illustration of an imaging device 1 for wound assessment with a graphical user interface according to an embodiment of the present invention. FIG. 2 is a hardware block diagram showing the structure of the imaging device 1. As shown in FIG. 1, the device 1 includes a graphical user interface or screen 15, which preferably includes a touch screen or panel 16 on a front side. The device 1 also includes one or more cameras 13, 14, preferably in the form of a two-dimensional (2D camera) 13 and a three-dimensional (3D) camera 14 on a back side. For example, the imaging device 1 may be a tablet computer, for example, an iPhone®, an iPad®, Android enabled devices and/or other various handheld mobile devise, which includes one or more cameras having the ability to capture and generate 3D images. As shown in FIG. 1, the device 1 may be a tablet or tablet-like device having the user interface or display 15 and an outer housing 30.

Electrical components are positioned within the housing. The electronic components may vary depending on the particular functionality of the device 1. However, by way of example, the electronic components may include, for example, a communication interface 17, a processor 11, and a memory 12 storing computer executable programs. The imaging device 1 may communicate with a data processing and storage server 2 via a network 19. The method described below may be implemented by computer executable programs stored on the imaging device 1 and/or or the server 2 executed by the processor of the imaging device and/or the server.

During wound image capture in preferred embodiments of the present invention, both the 2D and 3D cameras are used to capture image data. For example, 3D images may be used to estimate the depth of the wound, and 2D images may be used to measure the size and color of the wound.

In a preferred embodiment, the 3D camera 14 is a structured-light 3D scanner that uses structured-light 3D scanning methods to obtain 3D data about objects. This is accomplished by projecting a pattern of light (e.g., visible or IR light) from the scanner onto the 3D surface of the object, and capturing the image (e.g., a video) of the light pattern on the object's surface using one or more sensors that have different perspectives than the light projector. Due to the shape of the 3D object and the different perspectives, the light pattern in the captured images will appear distorted as compared to the original projected pattern; such information is used to exact geometric information of the object surface. These 3D scanners are fast; some can scan an entire field of view in less a second. Structured-light 3D scanners are available commercially. Any suitable structured-light 3D scanners may be used to implement embodiments of the present invention.

The structured-light 3D scanner used in embodiments of the invention can automatically determine the distance of the object at the center of the view in order to properly adjust the setting of its sensors and/or optics to successfully capture the 3D data. However, the inventors discovered that when the wound located at the center of the view has a shiny surface, the 3D scanner often fails to determine the distance and therefore unable to properly capture the 3D data.

Embodiments of the present invention provide a wound image capture method that achieves two goals: First, to measure moisture level of wound as a wound assessment value; and second, to improve the quality of the captured images, including 3D images, which are used to assess other aspects of the wound. Image capture methods according to the present embodiments use the responses of the cameras to the different intensities of the incident illumination light to estimate the moisture level of a wound, in the meantime to help obtain correct wound measurement even when the wound is wet due to blood or pus.

Figure 3:
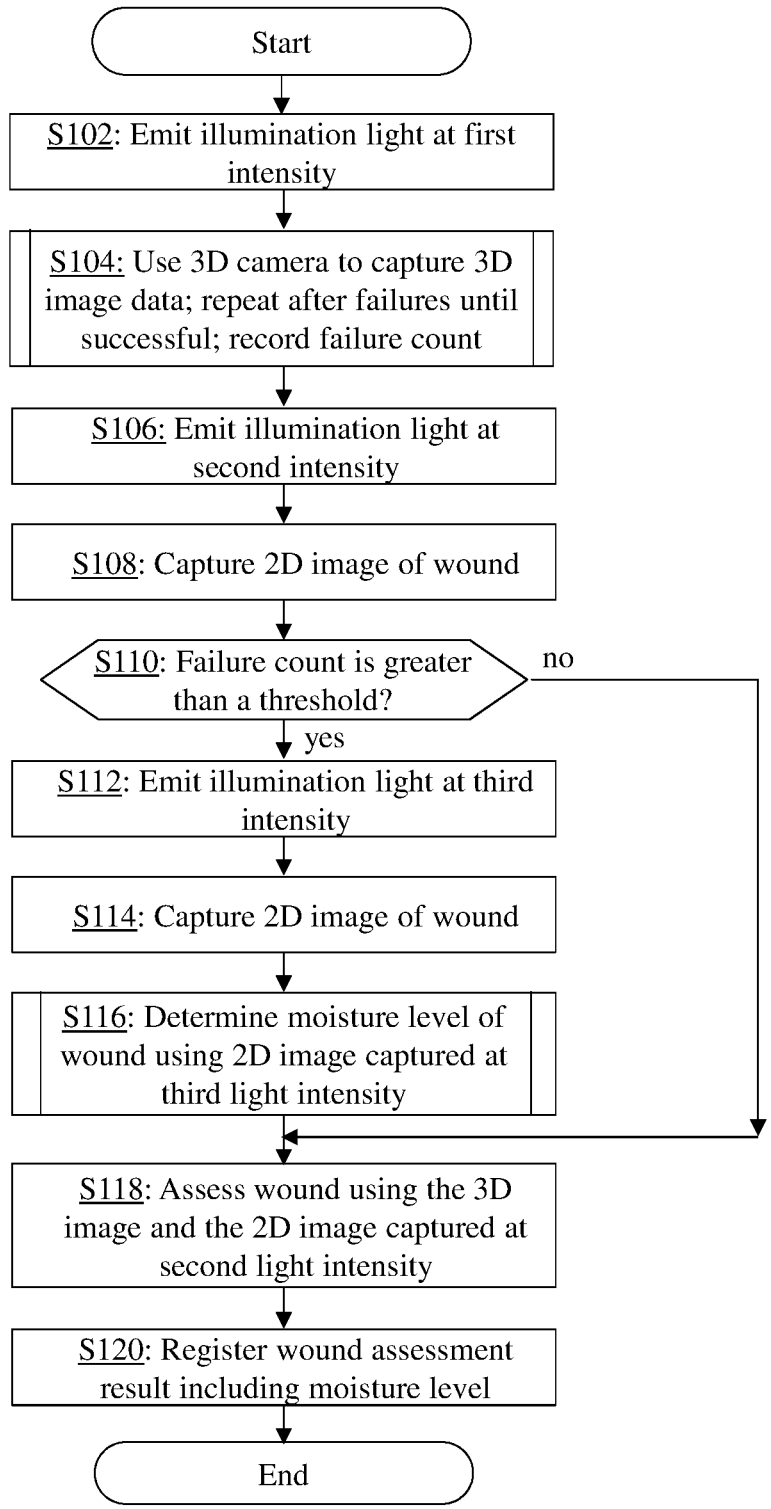
FIG. 3 schematically illustrates a wound image capture and wound assessment process according to a first embodiment of the present invention.

FIG. 3 schematically illustrates a wound image capture and wound assessment process according to a first embodiment of the present invention. As shown in FIG. 3, at the beginning of the process, the user uses the 3D camera to capture a 3D image of the wound (step S104). This steps includes repeatedly attempting the 3D image capture until the camera can properly determine the distance of the object and capture the 3D image; the number of failures in that process is recorded. This step is performed with a first illumination light intensity (step S102). The illumination light is provided by a light source of the image capture device 1, for example, a light source 13*a* associated with the 2D camera 13. The first light intensity is preferably a medium or default light intensity level of the light source 13*a*, or is lower than the medium or default level. Alternatively, an additional light source can be attached to the image capture device 1 or used separately.

In the preferred embodiment, the 3D scanner 14 is controlled by its internal programs so that when 3D data capture is unsuccessful due to inability to determine the distance of the object or other reasons, it automatically repeats the image capture procedure. The 3D scanner will continue to attempt to capture 3D data while displaying messages or other types of indication on the user interface (the preview screen) to indicate the status of 3D data capture, for example to indicate that capture is in progress, or that a capture attempt did not succeed, or that a capture has been successful, or to suggest that the user moves the aim of the 3D scanner slightly, etc.

Figure 4:
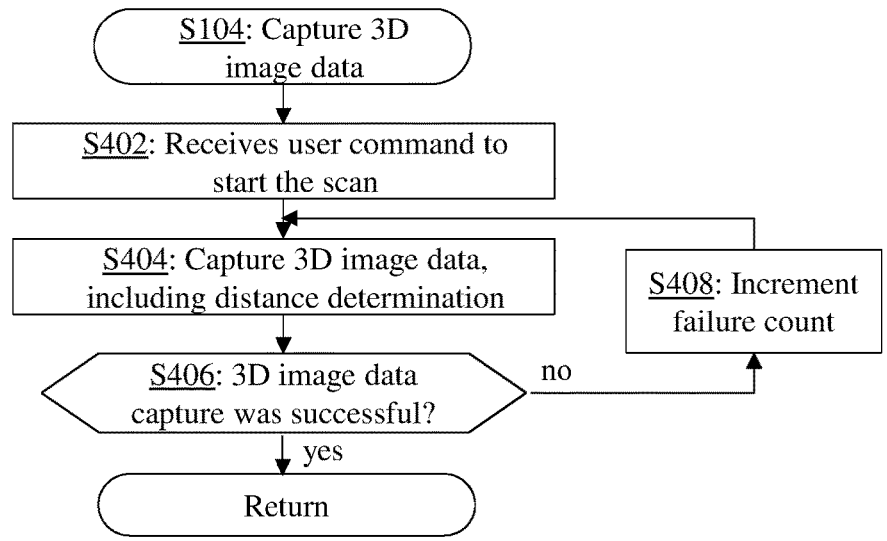
FIGS. 4 and 5 schematically illustrate the details of some of the steps in the process of FIG. 3.

In operation of step S104, as shown in FIG. 4, the user initiates the 3D scanning mode of the image capture device 1, holds the device and aims the 3D camera at a part of the patient's body that contains the wound, placing the wound at the center of the preview screen, and presses a "scan" or "start" button on the user interface (e.g. touch screen) (step S402). The image capture device performs the 3D imaging procedure, such as the structured-light 3D scanning procedure, including attempting to determine the distance of the object (wound surface) located near the center of the view (step S404). If the image capture device successfully captures the 3D data ("yes" in step S408), the failure count is stored and the process returns. As a part of the successful capture process, the image capture device analyzes the captured data to generate a 3D construction of the wound.

If the image capture device is unable to successfully capture the 3D data ("no" in step S408), which may be due to its inability to determines the distance of the wound surface or due to other reasons, the image capture device increments the failure count (step S406), and repeats the 3D data capture (step S404). In one embodiment, the image capture device emits a sound or displays an indication on the preview screen and automatically restarts the scan, so the user is informed of a failed data capture attempt. In another embodiment, the image capture device may display an indication on the preview screen about a failed data capture attempt and waits for the user to press a button to restart the scan. In either embodiment, the user may slightly move the aim of the 3D scanner when a failure indication is displayed to improve the capture condition.

The number of failures during the 3D data capture step S104 serves as an indication of whether the wound has a wet surface making 3D data capture difficult. A relatively high number of failures indicates presents of wet surface.

After the image capture device successfully captures the 3D image data and analyzes the data to generate a 3D construction of the wound (step S104 returns successfully), the image capture device emits an illumination light of the second intensity (step S106), and captures a 2D image of the wound using the 2D camera 13 (step S108). The second light intensity is preferably lower than the medium or default light intensity level of the light source 13*a*, or at the medium or default level. This step may include capturing multiple images at different exposure levels using the high dynamic range (HDR) mode of the 2D camera, so that the multiple images may be processed to generate an HDR image. HDR techniques are generally known in the art. Alternatively, the 2D image capture step may be repeated multiple times using different illumination light intensities to capture the images with different dynamic range and thus a wider dynamic range of image can be generated. The 2D image obtained in step S108 is used for wound assessment in step S118.

In an alternative embodiment, if the number of failures during 3D data capture does not exceed a predefined threshold T1 (e.g., 5 failures), then using HDR techniques is optional in the 2D image capture step S108. I.e., in this alternative embodiment, in step S108, image capture for HDR processing is preferably performed when the wound potentially has a wet surface. This can simplify the process when the wound does not have a wet surface.

Then, if the number of failures during 3D data capture exceeds the predefined threshold T1 ("yes" in step S110), the image capture device emits an illumination light of the third intensity (step S112), and captures a 2D image of the wound using the 2D camera 13 (step S114). The third light intensity is higher than the medium or default light intensity level of the light source 13a. In one embodiment, the third illumination light is a photographic flash light generated by the light source 13a.

The image capture device then performs a process of determining the moisture level of the wound using the 2D image captured under the third (higher) illumination light intensity (step S116). The details of this step are shown in FIG. 5.

Figure 5:
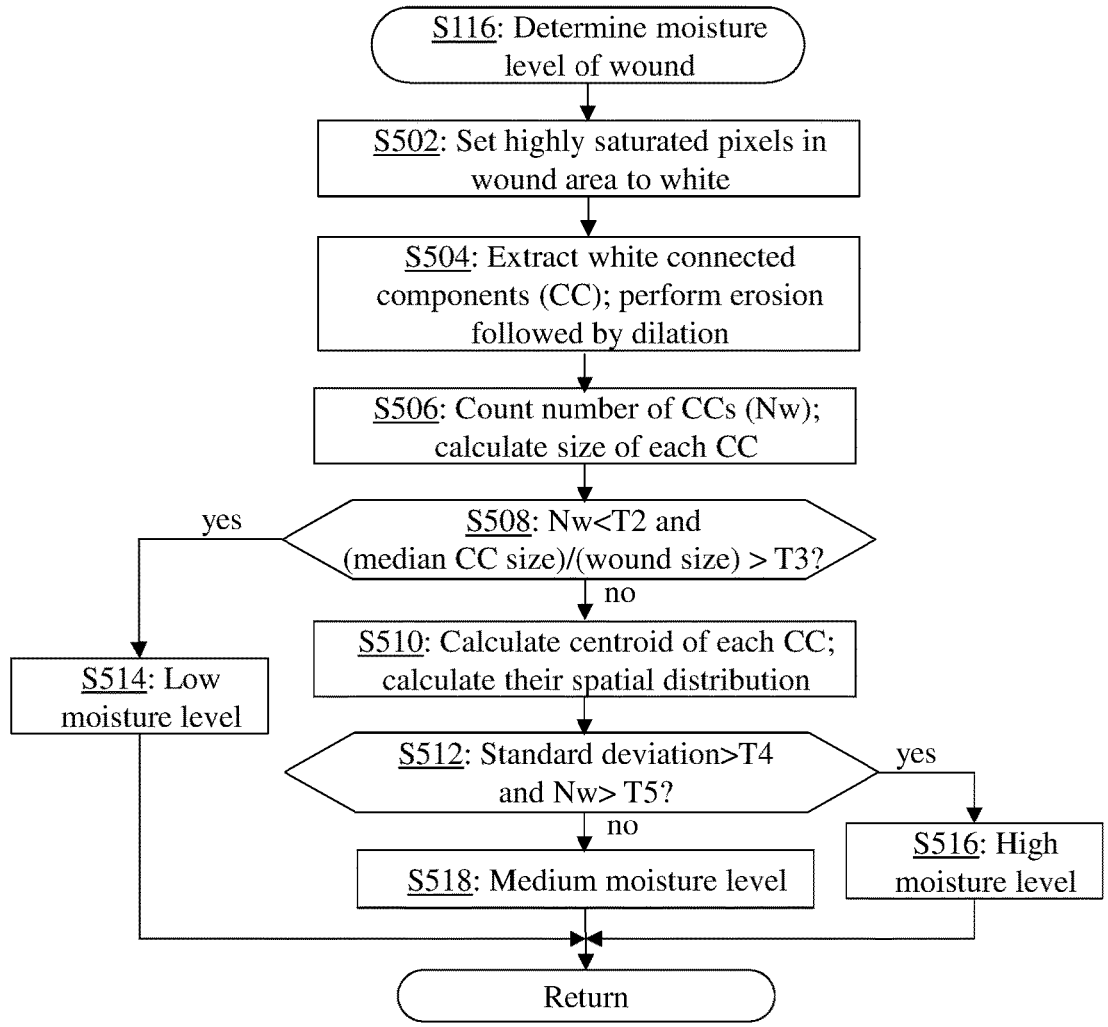

First, a preliminary step of wound area detection and extraction is performed (not shown in FIG. 5). The detection may be based on color and/or texture. This step may be done using the 2D image captures under the third illumination light intensity in step S114, or preferably using the 2D image captures under the second illumination light intensity in step S108. The steps shown in FIG. 5 are performed on the extracted would area of the 2D image.

In the extracted wound area, highly saturated pixels are set to white (step S502). This may be done by pixel value clustering on a color image or binarization on a grayscale image. For a color image, clustering is performed on the color values of the pixels to classify the color values into two or more classes (using any suitable clustering algorithm), and pixel values that belong to the class that is the closest to the white color value are changed to white.

After setting some pixels to white, connected component analysis is performed to extract white connected components in the image, where each white connected component is a group of white pixels that are connected to each other (step S504). Step S504 optionally includes performing an erosion operation so that small connected components (which are likely to be noise) are eliminated, followed by a dilation operation so that closely adjacent connected components are connected together.

The number of white connected components (Nw) is then counted, and the size (i.e. area) of each white connected component is calculated (step S506). If the number of white connected components Nw is less than a predefined threshold T2 (for example, T2=3), and the ratio of the median size of the white connected components to the size (i.e. width*height) of the wound area is greater than a predefined threshold T3 (for example, T3=20%) ("yes" in step S508), then the moisture level of the wound is determined to be low (step S514).

Otherwise ("no" in step S508), the centroid location of each white connected component is calculated, and the spatial distribution of the centroids is calculated (step S510). If the standard deviation of the spatial distribution is greater than a predefined threshold T4 (for example, T4=0.5), and the number of white connected components Nw is greater than another predefined threshold T5 (for example, T5=10) ("yes" in step S512), then the moisture level of the wound is determined to be high (step S516). Otherwise ("no" in step S512), the moisture level of the wound is determined to be medium (step S518). This concludes the moisture level assessment process S116.

It can be seen that the algorithm in step S116 (FIG. 5) is based on the observation that under a more intense illumination light, wet areas will be shiny and hence have a relatively large number of bright or saturated pixels. In addition, the bright or saturated pixels are scatted due to the uneven wound surface.

Referring back to FIG. 3, wound assessment is performed using the 3D image captured in step S104 and the 2D image captured at the second (lower) illumination light intensity in step S108 (step S118). Wound assessment may include measuring the length, width, depth, volume, color, texture, etc. of the wound. Any suitable methods may be used to perform the wound assessment. Then, the wound assessment results, including the results obtained from step S118 and the moisture level assessment obtained from step S116, are registered in a database along with other information such as the patient's name, the nurse's name, date and time, etc.

Figure 6:
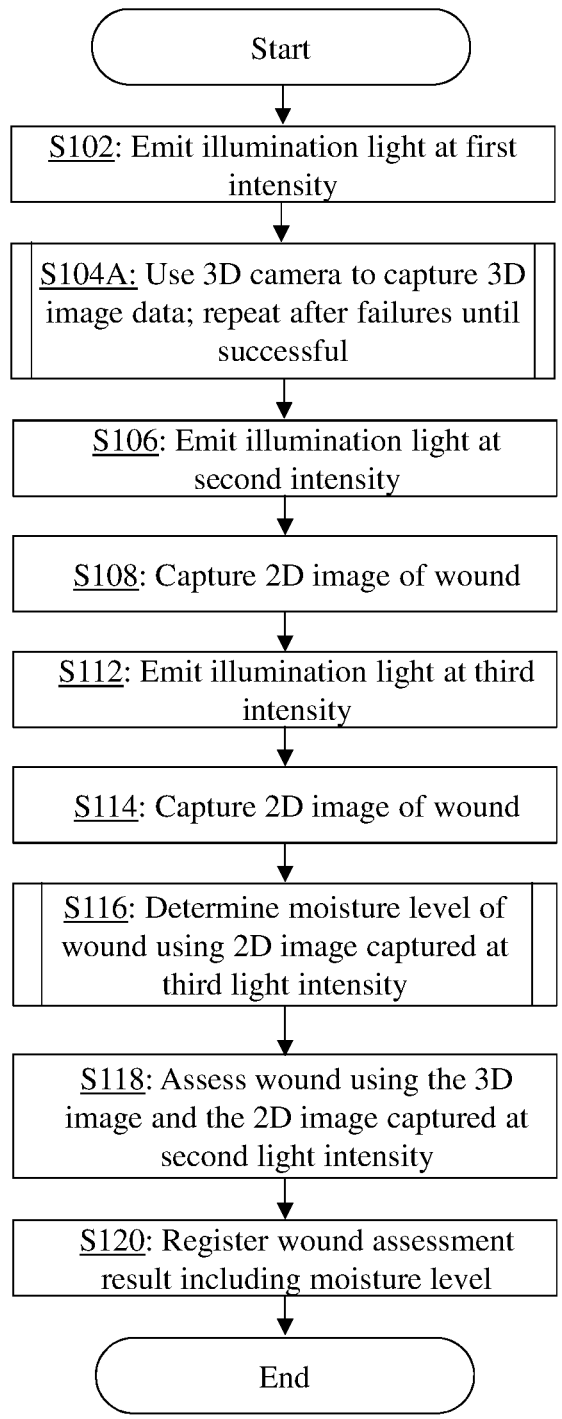
FIG. 6 schematically illustrates a wound image capture and wound assessment process according to a second embodiment of the present invention.

FIG. 6 schematically illustrates a wound image capture and wound assessment process according to a second embodiment of the present invention. This process is identical to the process of the first embodiment (FIG. 3) except: (1) The 3D image capture step S104A in FIG. 6 is similar to step S104 (FIG. 4) but the failure count is not necessary; and (2) step S110 in FIG. 3 is eliminated, i.e., steps S112, S114 and S116 are always performed regardless of the failure count.

Figure 7:
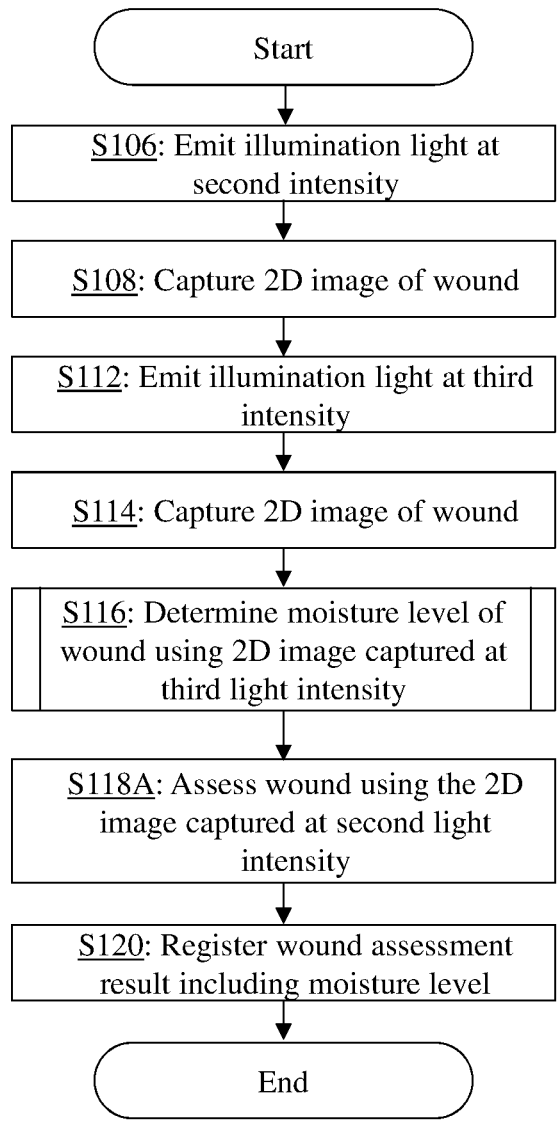
FIG. 7 schematically illustrates a wound image capture and wound assessment process according to a third embodiment of the present invention.

FIG. 7 schematically illustrates a wound image capture and wound assessment process according to a third embodiment of the present invention. This process is identical to the process of the second embodiment (FIG. 6) except: (1) The 3D image capture step (S102, S104A) is eliminated; and (2) the wound assessment step S118A in FIG. 7 is similar to step S118 in FIGS. 3 and 6 but does not use 3D image data.

In embodiments of the present invention, the third illumination light intensity is always higher than the second illumination light intensity and the first illumination light intensity (if it is used). A common feature of the first, second and third embodiments is that they use a relatively high illumination light intensity (which may be a flash) to acquire a 2D image containing a large number of saturated pixels to perform moisture level assessment, and use a relatively low illumination light intensity to acquire a 2D image for other aspects of wound assessment such as size, color, etc.

The wound image capture and wound assessment processes of the first to third embodiments of the present invention are implemented using the image capture device 1. Various steps of the processes, such as the emitting of the illumination lights (steps S102, S106, S112) and capture of the 3D and 2D images (steps S104, S108 and S114), may require initiation by the user, and the image capture device may display various prompts on the user interface screen 15, 16 or prompt the user to perform the next step.

It will be apparent to those skilled in the art that various modification and variations can be made in the wound image capture and assessment method and related apparatus of the present invention without departing from the spirit or scope of the invention. Thus, it is intended that the present invention cover modifications and variations that come within the scope of the appended claims and their equivalents.

What is claimed is:

1. A method implemented in a system including an image capture device for estimating moisture level of a wound of a patient, comprising:
   (a) capturing an image of a part of the patient's body which contains the wound while illuminating the part of the patient's body by a light of a predetermined intensity;
   (b) extracting a wound area from the image, the wound area including a plurality of image pixels each having a pixel value; and (c) estimating the moisture level of the wound based on a subset of the plurality of image pixels in the wound area which have pixel values within a defined range, including:
 (c1) setting all image pixels in the wound area that have pixel values within the defined range to white;
 (c2) extracting white connected components in the wound area, each white connected component being a group of image pixels in the wound area that have been set to white and that are spatially connected to each other; and
 (c3) estimating the moisture level of the wound based on the white connected components; and
(d) registering the estimated moisture level in a database.

2. The method of claim 1, wherein each image pixel has a color value, wherein step (c1) includes:
 performing a clustering operation on color values of pixels in the wound area to classify the color values into two or more classes; and
 setting pixels whose color values belong to a class that is the closest to a white color value to white.

3. The method of claim 1, wherein step (c1) includes:
 generating a grayscale image of the wound area from the captured image; and
 binarizing the grayscale image to set each pixel in the wound area to either black or white.

4. The method of claim 1, wherein step (c2) further comprises:
 performing an erosion operation and then a dilation operation on the white connected components.

5. The method of claim 1, wherein step (c3) includes estimating the moisture level of the wound based on a number of the white connected components, sizes of the white connected components, and a distribution of locations of the white connected components.

6. The method of claim 1, wherein step (c3) includes:
 when a number of the white connected components is less than a first predefined threshold and a ratio of a median size of the white connected components to a size of the wound area is greater than a second predefined threshold, the moisture level of the wound is estimated to be low; and
 when the moisture level of the wound is not estimated to be low, and when a standard deviation of a spatial distribution of centroids locations of the white connected components is greater than a third predefined threshold and the number of white connected components is greater than a fourth predefined threshold, the moisture level of the wound is estimated to be high.

7. The method of claim 1, wherein the light of the predetermined intensity is a photographic flash light.

8. An image capture device comprising:
 a camera for capturing images;
 a user interface screen for displaying images and information and for interacting with a user;
 a processor; and
 a computer usable non-transitory memory having a computer readable program code embedded therein which is configured to be executed by the processor to control the camera and the user interface, and to perform a process of estimating moisture level of a wound of a patient, the process comprising:

(a) capturing an image of a part of the patient's body which contains the wound while illuminating the part of the patient's body by a light of a predetermined intensity;
(b) extracting a wound area from the image, the wound area including a plurality of image pixels each having a pixel value; and
(c) estimating the moisture level of the wound based on a subset of the plurality of image pixels in the wound area which have pixel values within a defined range, including:
 (c1) setting all image pixels in the wound area that have pixel values within the defined range to white;
 (c2) extracting white connected components in the wound area, each white connected component being a group of image pixels in the wound area that have been set to white and that are connected to each other; and
 (c3) estimating the moisture level of the wound based on the white connected components; and
(d) registering the estimated moisture level in a database.

9. The image capture device of claim 8, wherein each image pixel has a color value, wherein step (c1) includes:
 performing a clustering operation on color values of pixels in the wound area to classify the color values into two or more classes; and
 setting pixels whose color values belong to a class that is the closest to a white color value to white.

10. The image capture device of claim 8, wherein step (c1) includes:
 generating a grayscale image of the wound area from the captured image; and
 binarizing the grayscale image to set each pixel in the wound area to either black or white.

11. The image capture device of claim 8, wherein step (c2) further comprises:
 performing an erosion operation and then a dilation operation on the white connected components.

12. The image capture device of claim 8, wherein step (c3) includes estimating the moisture level of the wound based on a number of the white connected components, sizes of the white connected components, and a distribution of locations of the white connected components.

13. The image capture device of claim 8, wherein step (c3) includes:
 when a number of the white connected components is less than a first predefined threshold and a ratio of a median size of the white connected components to a size of the wound area is greater than a second predefined threshold, the moisture level of the wound is estimated to be low; and
 when the moisture level of the wound is not estimated to be low, and when a standard deviation of a spatial distribution of centroids locations of the white connected components is greater than a third predefined threshold and the number of white connected components is greater than a fourth predefined threshold, the moisture level of the wound is estimated to be high.

14. The image capture device of claim 8, wherein the light of the predetermined intensity is a photographic flash light.

* * * * *